United States Patent
Jaffe et al.

(12) United States Patent (10) Patent No.: US 8,166,971 B2
(45) Date of Patent: May 1, 2012

(54) END-TIDAL GAS ESTIMATION SYSTEM AND METHOD

(75) Inventors: Michael B. Jaffe, Cheshire, CT (US); Joseph A. Orr, Park City, UT (US)

(73) Assignee: RIC Investments, LLC, Wilmington, DE (US)

( * ) Notice: Subject to any disclaimer, the term of this patent is extended or adjusted under 35 U.S.C. 154(b) by 1085 days.

(21) Appl. No.: 12/046,808

(22) Filed: Mar. 12, 2008

(65) Prior Publication Data

US 2008/0228096 A1     Sep. 18, 2008

Related U.S. Application Data

(60) Provisional application No. 60/918,189, filed on Mar. 15, 2007.

(51) Int. Cl.
*A61M 11/00*     (2006.01)

(52) U.S. Cl. .......... 128/204.23; 128/204.21; 128/204.18

(58) Field of Classification Search ............. 128/204.23, 128/204.18, 204.21, 200.14, 200.23, 203.15; 600/532, 529, 538, 543
See application file for complete search history.

(56) References Cited

U.S. PATENT DOCUMENTS

| | | | |
|---|---|---|---|
| 5,485,827 A * | 1/1996 | Zapol et al. | 128/200.14 |
| 5,632,281 A | 5/1997 | Rayburn | |
| 5,800,361 A * | 9/1998 | Rayburn | 600/532 |
| 6,024,089 A | 2/2000 | Wallace et al. | |
| 6,955,651 B2 | 10/2005 | Kuck et al. | |
| 2002/0174866 A1 | 11/2002 | Orr et al. | |
| 2003/0045807 A1 | 3/2003 | Daniels, II et al. | |
| 2005/0177055 A1 | 8/2005 | Kuck et al. | |
| 2008/0009762 A1 | 1/2008 | Hampton et al. | |
| 2008/0091117 A1* | 4/2008 | Choncholas et al. | 600/538 |

* cited by examiner

*Primary Examiner* — Steven Douglas (57) ABSTRACT

An apparatus and method of indicating the reliability of an end-tidal gas value that includes measuring a plurality of gas concentration values, measuring a plurality of ventilation values, determining an end-tidal gas value from the gas concentration values, determining the degree of ventilatory stability from the ventilation values, and providing an estimate of reliability of the end-tidal gas values using the degree of ventilatory stability.

19 Claims, 7 Drawing Sheets

END-TIDAL GAS ESTIMATION SYSTEM AND METHOD

CROSS-REFERENCE TO RELATED APPLICATIONS

This application claims priority under 35 U.S.C. §119(e) from provisional U.S. patent application No. 60/918,189, filed Mar. 17, 2007, the contents of which are incorporated herein by reference.

BACKGROUND OF THE INVENTION

1. Field of the Invention

The present invention pertains to a method and apparatus for providing a reliable end-tidal carbon dioxide ($CO_2$), end-tidal oxygen ($O_2$), or other gas estimation.

2. Description of the Related Art

Respiratory gas monitoring systems typically comprise gas sensing, measurement, processing, communication, and display functions. Such systems are considered to be either diverting (i.e., sidestream) or non-diverting (i.e., mainstream). A diverting gas measurement system transports a portion of the sampled gases from the sampling site, which is typically a breathing circuit or the patient's airway, through a sampling tube, to the gas sensor where the constituents of the gas are measured. A non-diverting gas measurement system does not transport gas away from the breathing circuit or airway, but measures the gas constituents passing through the breathing circuit.

Conventional non-diverting gas measurement systems include gas sensing, measurement and signal processing required to convert the detected or measured signal (e.g., voltage) into a value that may be used by the host system. The gas measurement system communicates with the sample cell placed at the breathing circuit and comprises the components required to output a signal corresponding to a property of the gas to be measured. Placement of the sample cell directly at the breathing circuit results in a "crisp" waveform that reflects in real-time the partial pressure of the measured gas, such as carbon dioxide or oxygen, within the airway. The sample cell, which is also referred to as a cuvette or airway adapter, is located in the respiratory gas stream, obviating the need for gas sampling and scavenging as required in a diverting gas measurement system.

Conventional diverting gas measurement systems utilize a relatively long sampling plastic tube connected to an adapter in the breathing circuit (such as a T-piece at the endotracheal tube or mask connector) or a nasal catheter. The sample gas is continuously aspirated from the breathing circuit or the sample site through the sampling tube and into the sample cell within the monitor at sample flow rates ranging from 50 to 250 ml/min. The location of the sampling port in the breathing varies and may range anywhere from an elbow connected to an endotracheal tube to the wye connector.

Both diverting and non-diverting gas measurement systems include sensors that measure the concentration and/or partial pressure of at least one of the gas components in the sampled gas passing through the sample cell. Two of the most commonly measured gases of clinical importance are carbon dioxide and oxygen. Both diverting and non-diverting gas measurement systems utilize sensors to measure the constituent gases such as carbon dioxide and oxygen.

To measure these gases, electro-optical assemblies are often employed. In the case of a carbon dioxide sensor and a number of other gas sensors, these assemblies includes a source that emits infrared radiation having an absorption band for carbon dioxide. The infrared radiation is usually transmitted along a path that is normal to the flow path of the gas stream being analyzed. Photodetectors are arranged to receive and measure the transmitted radiation that has passed through the gas in the gas stream. Carbon dioxide within the sample gas absorbs this radiation at some wavelengths and passes other wavelengths. The transmitted radiation is converted to signals from which a processor calculates the partial pressure of carbon dioxide. In the case of an oxygen sensor, electrochemical or fluorescence based technologies are often employed.

Carbon dioxide and oxygen are expressed either as a gas fraction ($FCO_2$ and $FO_2$) or partial pressure ($PCO_2$ and $PO_2$). Capnography and oxygraphy, when used without qualification, refers to time-based capnography and oxygraphy. In addition to capnometry, capnography includes a plot of the instantaneous carbon dioxide concentration over the course of a respiratory cycle. From this plot, the cyclic changes can be visualized.

Figure 1:
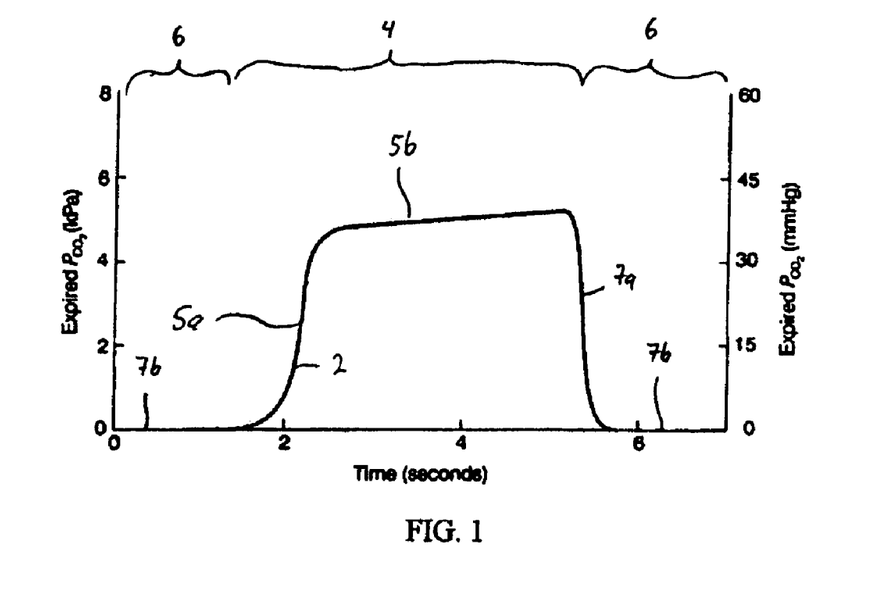
FIG. 1 is a graph of an exemplary time-based capnogram.

In a "textbook" capnogram 2, an example of which is shown in FIG. 1, the capnogram comprises two segments: an "expiratory" segment 4, and an "inspiratory" segment 6. The expiratory segment consists of a varying upslope 5a that levels to a constant or slight upslope 5b. The inspiratory segment consists of a sharp downslope 7a that settles to a plateau of negligible inspired carbon dioxide 7b. However, other than the end-tidal partial pressure of carbon dioxide, which has been generally understood as the partial pressure of carbon dioxide at the end of expiration, only breathing frequency and a measure of inspiratory carbon dioxide levels are clinically reported. This is the case because only the transition between the expiratory and inspiratory segments can usually be well delineated from a capnogram.

Even then, only if there is substantially no rebreathing, does this transition correspond to the time of the actual beginning of inspiration as delineated by the flow waveform. The transition between inspiration and expiration cannot be readily discerned because of the presence of anatomic dead space that fills with inspiratory gas at the end of expiration. Although the oxygram is not in as widespread clinical use as capnograph, the same issues discussed above apply to the oxygram with the understanding that the oxygram can be considered an inverted version of the capnogram.

Figure 2:
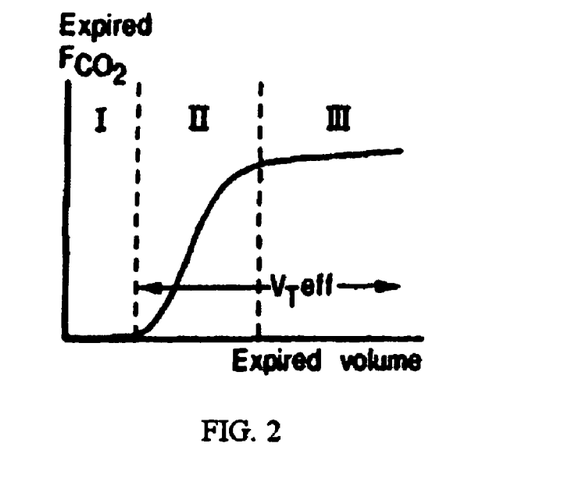
FIG. 2 is a graph of an exemplary volumetric capnogram.

If flow is measured in addition to carbon dioxide, the volumetric capnogram can be determined. Similarly if flow is measured in addition to oxygen, the volumetric oxygram can be determined. FIG. 2 illustrates the three phases of a volumetric capnogram. Phase I comprises the carbon dioxide free volume, while phase II comprises the transitional region characterized by a rapidly increasing carbon dioxide concentration resulting from progressive emptying of the alveoli. Phases II and III together are the carbon dioxide containing part of the breath, the effective tidal volume, $V_T$eff. Phase III, the alveolar plateau, typically, has a positive slope indicating a rising $PCO_2$. Using these three phases of the volumetric capnogram, physiologically relevant measures, such as the volumes of each phase, the slopes of phase II and III, and carbon dioxide elimination, as well as deadspace tidal volume and ratios of anatomic and physiologic deadspace can be determined.

One of the objectives when setting the level of mechanical ventilation for a patient is to reach and maintain a desired concentration of arterial carbon dioxide concentration ($PaCO_2$). Because real-time access to $PaCO_2$ measurements is not easy, estimates from a capnogram are used to obtain a surrogate measure. Because of pulmonary shunting, i.e., a portion of the right heart cardiac output reaches the left atrium without having participated in gas exchange, the closest surrogate of $PaCO_2$ that can be obtained from the capnogram is alveolar $CO_2$ concentration ($PACO_2$).

The end-tidal partial pressure of $CO_2$ ($PetCO_2$), usually referred to as the end-tidal carbon dioxide, is used clinically, for example, to assess a patient ventilatory status and, as noted above, has been used by some as a surrogate for $PaCO_2$. Similarly, the end-tidal partial pressure of $O_2$ ($PetO_2$), which may be referred to as the end-tidal oxygen, is also used.

The medical literature is replete with conflicting articles regarding the relationship between $PetCO_2$ and $PaCO_2$, as well as the relationship between changes in $PetCO_2$ and changes in $PaCO_2$. On one hand, Nangia et al. notes that "$ETCO_2$ correlates closely with $PaCO_2$ in most clinical situations in neonates". Similarly, Wu et. al. notes that "we recommend using mainstream capnography to monitor $PetCO_2$ instead of measuring $PaCO_2$ in the NICU." On the other hand, Russell et al. studied ventilated adults and noted "trends in $P(a-et)CO_2$ magnitude are not reliable, and concordant direction changes in $PetCO_2$ and $PaCO_2$ are not assured."

Researchers have considered maneuvers to improve 'prediction' of $PaCO_2$. Tavernier et al. studied whether prolonged expiratory maneuvers in patients undergoing thoracoabdominal oesophagectomy improved the prediction of $PaCO_2$ from $PetCO_2$ and concluded that these maneuvers did not improve estimation. A commonly held belief among critical care physicians is that end-tidal $CO_2$ cannot be used as a surrogate for either arterial $PCO_2$ or changes in arterial $PCO_2$. To complicate matters further Chan et al. noted that "mainstream $PetCO_2$ provided a more accurate estimation of $PaCO_2$ than side-stream measurement."

If end-tidal $PCO_2$ could be reliably used as a surrogate for arterial $CO_2$, arterial blood sampling could be reduced, applications that currently use intermittent blood sampling would become more clinically acceptable, and applications, such as closed loop control of ventilation (particularly non-invasive ventilation), would be more viable. Therefore, techniques for reliability and/or indicating the reliability of end-tidal $PCO_2$ estimations are desired.

SUMMARY OF THE INVENTION

Accordingly, it is an object of the present invention to provide a method of indicating the reliability of an end-tidal gas value that overcomes the shortcomings of conventional end-tidal $CO_2$ measurement techniques. This object is achieved according to one embodiment of the present invention by providing a method of indicating the reliability of an end-tidal gas value that includes measuring a plurality of gas concentration values, measuring a plurality of ventilation values, determining an end-tidal gas value from the gas concentration values, determining the degree of ventilatory stability from the ventilation values, and providing an estimate of reliability of the end-tidal gas values using the degree of ventilatory stability.

It is a further object of the present invention to provide an apparatus that indicates the reliability of an end-tidal gas value that overcomes the shortcomings of conventional end-tidal $CO_2$ measurement techniques. This object is achieved according to one embodiment of the present invention by providing an apparatus comprising a means for sensing a plurality of gas concentration values, means for sensing a plurality of ventilation values, means for determining an end-tidal value from the gas concentration values, means for determining the degree of ventilatory stability from the ventilation values, and means for providing an estimate of reliability of the end-tidal gas values using the degree of ventilatory stability.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

The present invention addresses the known problems with the studies to date including (a) the lack of a clear definition of end-tidal gas value, (b) how end-tidal gas values relate to arterial gas values in both 'stable' and 'unstable' ventilatory patterns, and, (c) an understanding of when end-tidal gas values will and won't be a reliable correlate of arterial and or alveolar gas values. The present invention addresses the need to provide more reliable end-tidal gas values. It should be noted that the while most of the present discussion takes place with reference to carbon dioxide ($CO_2$), the methods described herein apply to other gases as well, including but not limited to respiratory gases, such as oxygen, nitrous oxide, nitric oxide, and other gases, such as anesthetic agents. To determine a more reliable end-tidal gas value, it is important to delineate properly the end-tidal gas value and to determine the reliability of that estimate.

Figure 3:
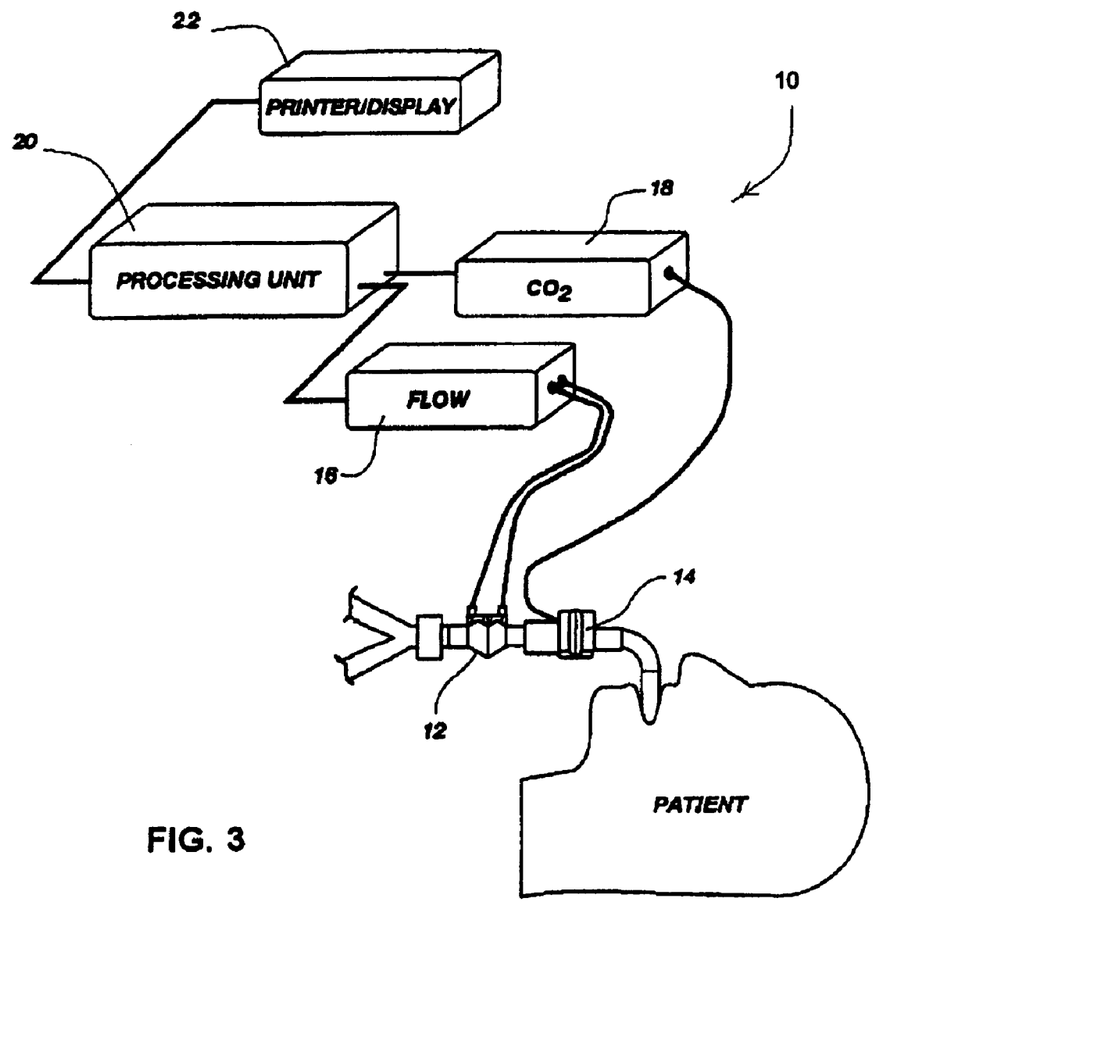
FIG. 3 is a schematic illustration of a gas measurement system in accordance with an exemplary embodiment of the present invention.

An exemplary embodiment of a gas measurement system 10 suitable for use in the present invention is illustrated in FIG. 3. The illustrated exemplary embodiment of system 10 comprises a differential pressure flowmeter 12, a flow signal unit 16, a gas sensor 14, a $CO_2$ signal unit 18, a processor or processing unit 20, and a data display 22. System 10 can be used alone or in combination with mechanical ventilation of the patient. It can be a stand-alone monitoring system or integrated with a ventilator.

The exemplary device for respiratory flow measurement is differential pressure flowmeter 12, which provides a pressure differential indicative of respiratory flow; the differential pressure being converted via pressure transducers in flow signal unit 16 to electrical signals representative of the relationship between respiratory flow and pressure differential. An exemplary differential pressure flowmeter is manufactured and sold by Respironics, Inc., Wallingford, Conn. However, any flow measurement devices may be utilized, including flow sensors based on other flow measurement techniques, such as optical, vanes, sonic, etc.

Sensors capable of measuring carbon dioxide content in a gas sample are well known. An exemplary device for measuring carbon dioxide content is a gas analyzer of the type employing non-dispersive infrared radiation, which presents data representing the % $CO_2$ (or $pCO_2$) of a sample of exhaled breath. Other technologies used to measure the concentration of carbon dioxide, such as electrochemical technologies, Raman spectroscopy, and mass spectroscopy, can also be used in the present invention. The exemplary gas sensor 14 capable of measuring carbon dioxide content in a patient's exhaled breath is available from Respironics, Inc., Wallingford, Conn., under the trade name CAPNOSTAT®. It is to be understood, however, that other methods of measuring carbon dioxide content, either at the airway (non-diverting) or by removing a sample (diverting), may be used in the present invention.

Figure 4:
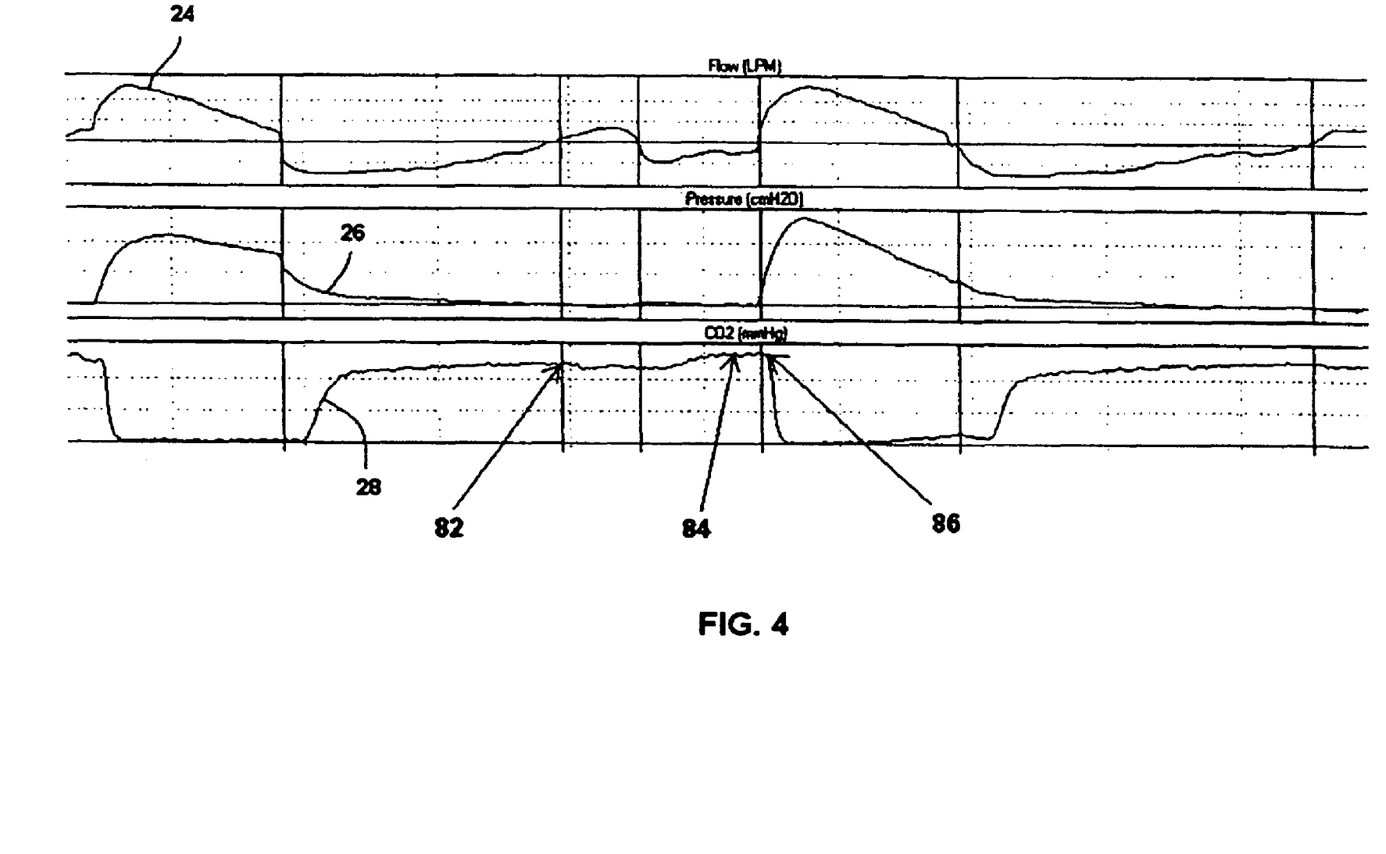
FIG. 4 is a chart illustrating flow, pressure, and $CO_2$ measurements of a patient.

FIG. 4 illustrates one of the problems determining a repeatable and reliable end-tidal value with a plot of flow 24, pressure, 26 and $CO_2$ 28 as a function of time for two "breaths" with ventilator-patient asynchrony. The measured value of the $PetCO_2$ depends upon how $PetCO_2$ value is defined. For example, depending on how end-tidal $CO_2$ is determined, it could be reported as either 27, 30 or 31 mm Hg. In FIG. 4, $PetCO_2$ at position 82 is 27 mm Hg, at position 84 is 31 mm Hg, and at position 86 is 30 mm Hg. The end of expiration, as defined by the flow waveform (position 82), results in an end-tidal value of 27 mm Hg. However, using the apparent expiration-inspiratory transition-position 86 from the capnogram alone results in $PetCO_2$ of 30 mmHg. On the other hand, if the largest value is used (position 84) a $PetCO_2$ of 31 mm Hg is obtained.

Conventionally, the concentration towards the end of phase III of the time or volumetric capnogram is considered the good estimator of alveolar $CO_2$ concentration (i.e. $PetCO_2$) and is usually determined on a breath-by-breath basis. As noted earlier, the simplest approach to determining $PetCO_2$ is simply to use the maximum value which would generally occur during phase III. Because extreme values are often sensitive to artifact or noise, other approaches may use an average over the last part of phase III, where the 'last part' can be defined either in terms of time or in terms of expiratory volume.

The present invention, unlike these other techniques, contemplates using the flow and/or pressure waveform to better delineate the end of expiration, especially, if significant rebreathing is present, so that the end-tidal gas value may be simply and repeatably determined. Similarly, because volume is the integral of flow, the volumetric capnogram may also be used as well to better delineate the end of expiration (see below). If the flow waveform or a surrogate is not available, the present invention contemplates using a waveform shape analysis to better delineate the end of expiration.

Figure 5:
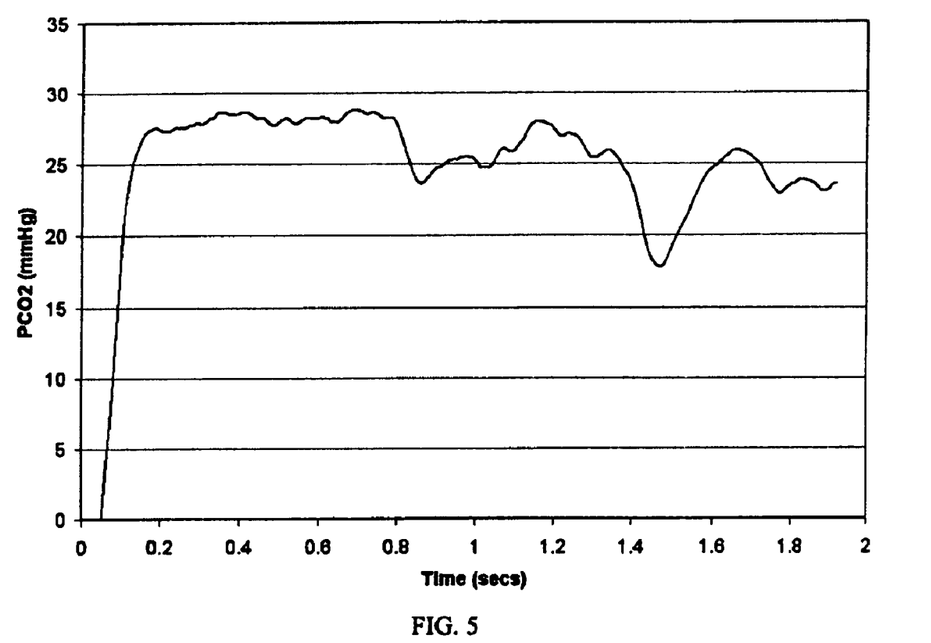
FIG. 5 is an exemplary time-based capnogram with a long expiratory pause.
Figure 6:
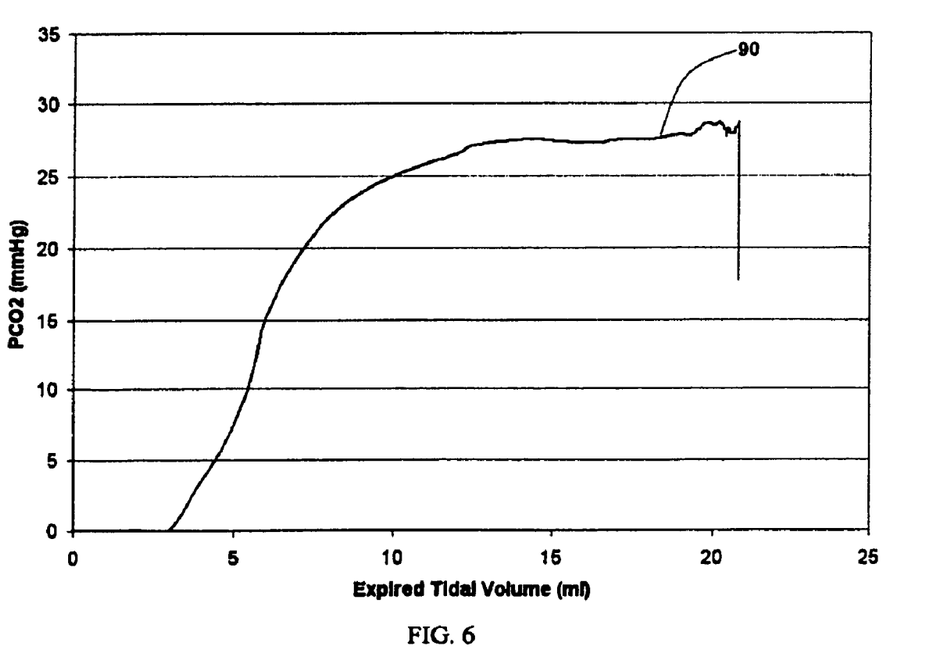
FIG. 6 is exemplary volumetric capnogram of the waveform in FIG. 5.

FIGS. 5 and 6 are time-based and volumetric capnograms illustrating the potential difficulty of obtaining an end-tidal value from a time based capnogram alone. FIG. 5 illustrates a phenomenon often seen in neonates with long expiratory pauses due to the I:E ratios of 1:8-1:10 during which very minor inspiratory efforts are made resulting in a capnogram that is difficult to interpret. Examining such a time-based capnogram makes it very difficult to determine an end-tidal value. However, comparing the time-based and volumetric-based capnograms in FIGS. 5 and 6 allows for some clarity. Note that the ventilation-perfusion relationships of the lung are more accurately reflected in the slope of phase III by a volumetric capnogram than in that of a time-based capnogram in which the gradient of the phase III slope is usually less obvious and can be misleading. This may be because a smaller volume of expired gases (approximately the final 15%) often occupies half the time available for expiration, so that a similar change in the $CO_2$ concentration is distributed over a greater length of time in the time-based capnogram than in the volumetric capnogram.

In FIG. 6, the plot of the expired volume vs. the partial pressure of $CO_2$ during expiration clearly shows a plateau 90 from which an end-tidal value may be determined using a variety of methods. All of the parameters associated with volumetric capnography can also be determined. For example, the end-tidal gas value may be determined by computing the average $PCO_2$ value for the last X % of volume (such as 5 or 10%), fitting the curve, or a portion of it, to a model (physiologically based such as one based on Weibel model or empirical). Using a model based approach to fit the concentration-volume curve allows for potentially clinically relevant values to be determined.

In addition to the challenges already outline, one of the primary challenges in the determination and clinical use of $PetCO_2$ values comes from an implied assumption, that $PetCO_2$ represents the average value of the alveolar $CO_2$ concentration ($P_ACO_2$). As $CO_2$ continues to pass from the blood into the alveolar gas phase during expiration, the alveolar $CO_2$ concentration rises during expiration. During inspiration, $CO_2$ free gas serves to dilute the alveolar gas and the alveolar $CO_2$ concentration decreases. The shape of the respiratory flow waveform (e.g., tidal volume, inspiratory to expiratory time ratio), the pulmonary capillary blood flow, the venous $CO_2$ concentration, the amount of deadspace, and the serial and alveolar deadspace affect the particular shape of the alveolar $CO_2$ concentration waveform. This shape, in turn, affects the average alveolar $CO_2$ concentration. The very last part of the expired volume that leaves the lungs, never reaches gas sensor 14, but remains in the anatomical and apparatus (serial) deadspace.

Figure 8A:
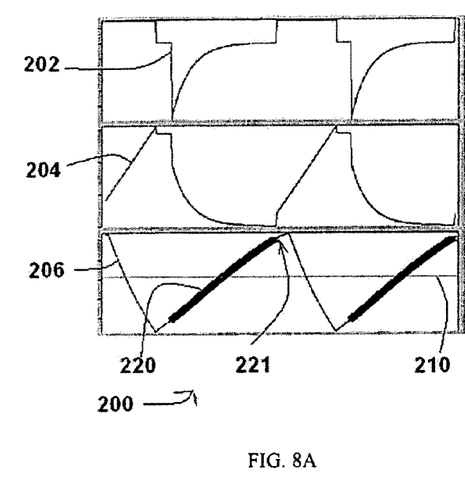
FIGS. 8A and 8B are plots of simulated flow, volume, and alveolar $CO_2$ concentrations.
Figure 8B:
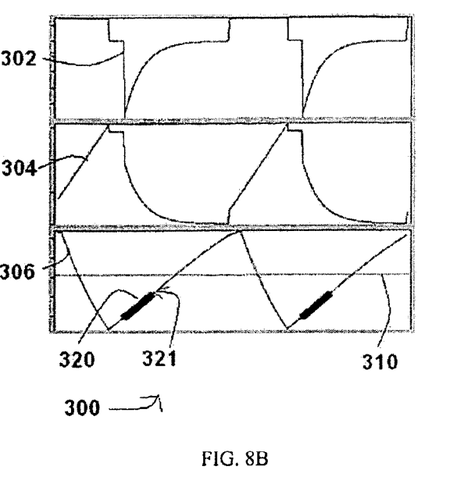

The simulation shown in FIGS. 8A and 8B, which show simulated flow 202, volume 204, and alveolar $CO_2$ concentration 206 waveforms illustrate how this can affect the $PetCO_2$ and its relationship to average alveolar $CO_2$ concentration. Lines 210 and 310 in alveolar $CO_2$ concentration graphs 206 and 306 indicate the average alveolar concentration. Thickened lines 220 and 320 of alveolar $CO_2$ concentration graphs 206 and 306 illustrate portions of the alveolar waveform that is measured by gas sensor 14 in the form of a capnogram. End portions 221 and 321 of the thickened lines 220 and 320 are conventionally reported as $PetCO_2$.

FIG. 8A illustrates the waveforms that would be observed if there was no serial deadspace between the alveoli and gas sensor 14. The resulting $PetCO_2$ value (end portion 221) would overestimate average alveolar $CO_2$ in this simulation. FIG. 8B illustrates the waveforms which would be observed if there was a normal serial deadspace (e.g., 150 ml) between the alveoli and gas sensor 14. The resulting $PetCO_2$ value (end portion 321) would underestimate average alveolar $CO_2$ in this simulation. The step size of the alveolar $CO_2$ concentration graphs 206 and 306 are approximately 4 mmHg. Larger deadspaces and smaller tidal volumes can increase the difference between $PetCO_2$ and average alveolar $CO_2$ concentration. Also, this effect may increase noise in $PetCO_2$ signal due to breath-to-breath variations in tidal volumes of spontaneously breathing patients.

Figure 9A:
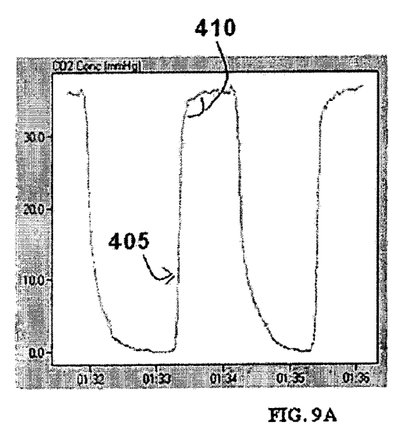
FIG. 9A is a time based capnogram recorded with a mouthpiece.
Figure 9B:
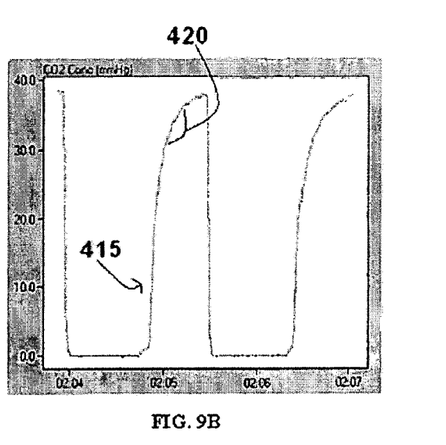
FIG. 9B is a time-based capnogram recorded with a face mask.

In patients who breathe through a face mask (instead of an endotracheal tube), the capnogram is additionally affected by the "smearing" effect of the face mask volume—again exacerbated by small or varying tidal volumes. This "smearing" effect is shown in FIGS. 9A and 9B. In FIG. 9A, the patient is breathing with through a mouthpiece resulting in alpha angle 410 of capnogram 405, which is only slightly larger than 90 degrees. In addition, capnogram 405 has as a relatively flat phase III. In FIG. 9B, the same patient is breathing through a face mask resulting in alpha angle 420 of capnogram 415 that is more obtuse than angle 410. In addition, phase III of capnogram 415 is more rounded than in capnogram 405, primarily due to the dilution and mixing in the deadspace volume of the face mask. Generally, the differences between $PetCO_2$ and average alveolar $CO_2$ concentration are relatively small in most subjects (e.g., on the order of 2 or 3 mmHg) without serious ventilation-perfusion abnormalities. If, however, $PetCO_2$ is used to extract additional information, such as with partial $CO_2$ rebreathing maneuvers, these small differences may become significant.

The present invention contemplates approximating expiratory volumetric capnograms using mathematical functions. This is especially helpful when attempting to obtain a capnogram under adverse conditions, such as those noted above, as well as in the presence of large noise (physiological and instrumental). An exemplary mathematical function that may be used to approximate an expiratory volumetric capnogram is a power function of the following form:

$$invCO_2 = f \times V_E^n,$$

where: $invCO_2 = CO_2 - maxCO_2$, $CO_2$ is the expired $CO_2$ as measured by the gas sensor, $V_E$ is the expired volume, f and n are approximation parameters, and $maxCO_2$ is constant $CO_2$ value, which is another approximation parameter.

The approximation parameters f and n can be found by known numerical methods, including linear regression of natural log ($invCO_2$) vs natural log (VE). The approximation parameter $maxCO_2$ can be found iteratively using known search algorithms or using more generalized least-squares algorithms than conventional linear regression.

Figure 10:
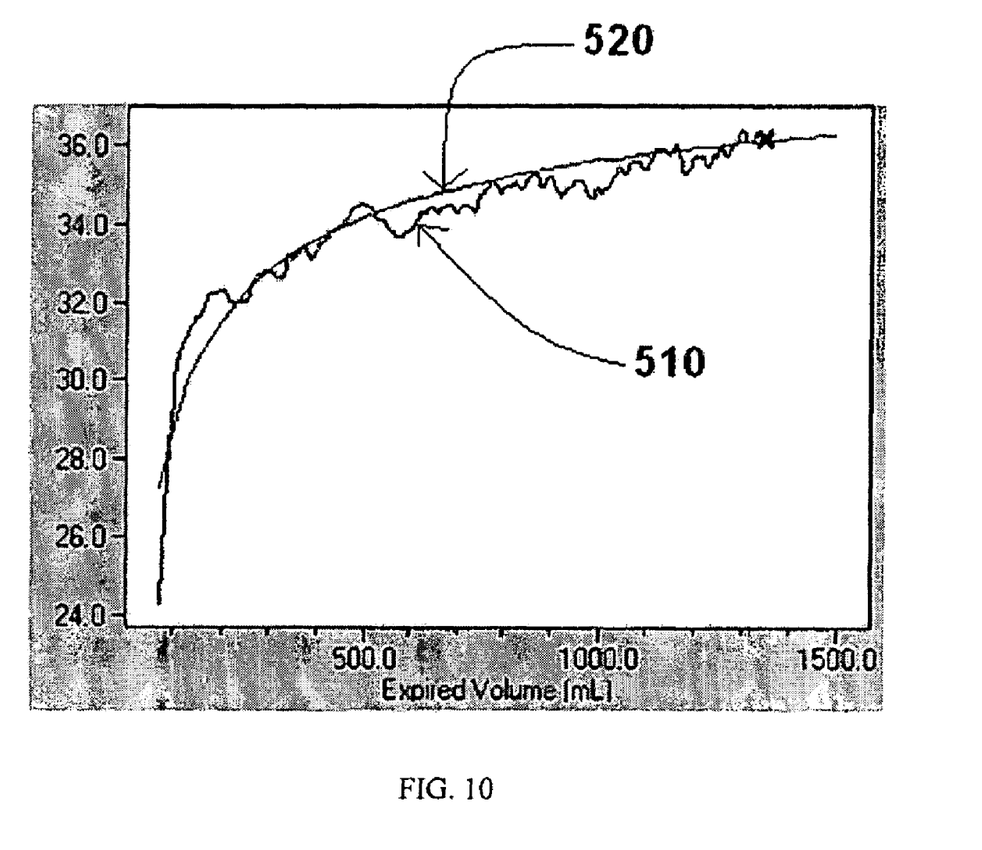
FIG. 10 is a volumetric capnogram and an associated power regression approximation curve.

FIG. 10 shows an example of an original capnogram 510 approximated by a power regression curve 520. A number of approaches are contemplated to determine an $PetCO_2$-equivalent value from this power regression approximation. In general, the $PetCO_2$ value should be more representative of the alveolar $CO_2$ concentration, if the tidal volume is large. If the tidal volume is small, the power regression approximation may be used to extrapolate to what the capnogram value would have been at a larger expiratory volume. Alternatively, the power regression approximation may be used to report the $PetCO_2$ concentration at one constant expired volume for all breaths, regardless whether they are small or large.

The present invention contemplates that the model derived $PetCO_2$ values could be used replace conventionally determined $PetCO_2$ values in conventional $CO_2$ monitors, as well as replace conventionally determined $PetCO_2$ values for differential $CO_2$ Fick determination of pulmonary capillary blood flow. Other approximation functions, other than the power function described above, are contemplated as well. The approximation parameters may be found by methods known in the art including, but not limited to, linear regression, least square algorithms, artificial neural networks and iterative search algorithms. The algorithm to find the approximation parameters may also consider approximation results from previous breaths to make finding the approximation parameters for the current breath faster, less computationally expensive, and more accurate.

Figure 7:
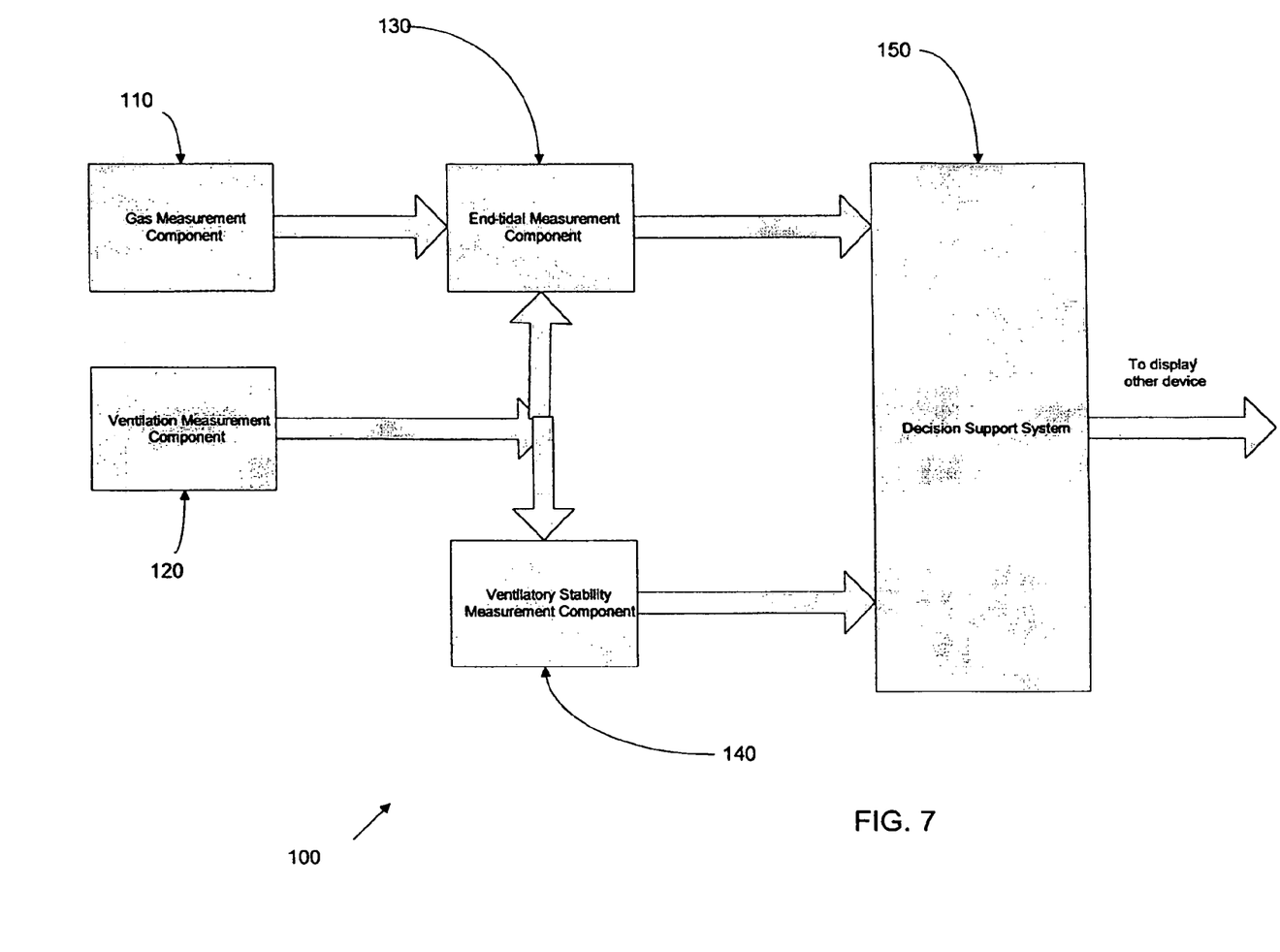
FIG. 7 is a schematic diagram of an exemplary apparatus suitable for implementing the process of the present invention.

The present invention contemplates providing a better definition of when end-tidal $CO_2$, however it may be determined, is a reliable/viable estimate of arterial $CO_2$ and when it is not a reliable/viable estimate of arterial $CO_2$. This may be related to both the physiological status of the patient's cardio-pulmonary system and the recent pattern of ventilation, which may have significantly affected the lung and blood stores of the patient. Therefore, estimation of $V_d/V_t$ physiologic/alveolar or a surrogate to assess the degree of impairment and the assessment of the degree of disturbance to the $CO_2$ stores would permit the end-tidal $CO_2$ value to be determined and displayed with greater confidence. FIG. 7, which is discussed in greater detail below, illustrates an exemplary process and apparatus for providing an indication of when end-tidal $CO_2$ is or is not a reliable/viable estimate of arterial $CO_2$.

The present invention also contemplates determining the degree of physiological impairment. Vd/Vt physiologic is preferably estimated using alveolar partial pressure of $CO_2$ ($P_ACO_2$) (per its definition without the Enghoff modification). $P_ACO_2$ may be estimated by application of models to the volumetric capnogram as well as neural networks, genetic algorithms, and other approaches or combination of approaches. U.S. Pat. No. 5,632,281 describes an approach for arterial estimation that may be used for alveolar estimation. VDalv/VTalv may be used as well and Hardman et al. describes a method for estimating this ratio.

The present invention also contemplates determining the degree of disturbance. The degree of disturbance or ventilatory stability can be assessed by different methods. For example, assessment of the degree of disturbance to the $CO_2$ stores may be determined by the measurement of ventilation (with the use of a model) to better determine periods of 'stability.' Methods of estimating $CO_2$ stores may be found in U.S. Pat. No. 6,955,651 ("the '651 patent"), the contents of which are incorporated herein by reference. The tidal volume must be sufficient size relative to the anatomic deadspace. Functional anatomic deadspace may be estimated by methods known in the art such as Fowler's method. The reliability of the end-tidal value is further increased by applying criteria based on the expiratory flow rate for the breath from which the end-tidal measurement is taken. Application of these criteria will help allow the determination of a reliable end-tidal value As noted above, FIG. 7 illustrates an exemplary schematic embodiment of a gas measurement system 100 according to the principles of the present invention. Gas measurement system 100 illustrates the components of a system used to provide a reliable estimate of the end-tidal concentration of a gas. The gas concentration or partial pressure values (used interchangeably) are determined by gas measurement component 110. This may be determined on a continuous or intermittent basis. Conventional gas concentration component provide data sampled at sampling rates from 25 to 100 samples/sec. Gas measurement component 110 corresponds, for example, to gas sensor 14 and $CO_2$ signal unit 18 in FIG. 1 as discussed above.

Ventilation values measured at the airway or via other technologies are determined by ventilation measurement component 120. Ventilation values includes, but are not limited to flow, volume, pressure, temperature, and humidity or any combination thereof. The ventilation values may be determined on a continuous or intermittent basis. Ventilation measurement component 120 corresponds, for example, to differential pressure flowmeter 12 and flow signal unit 16. In an exemplary embodiment, the ventilation related values are determined by measurements of flow, volume, or surrogates thereof. Surrogates of flow derived from acoustic measurements from external surface sensors from companies, such as Andromed, are contemplated.

The gas concentration values from gas measurement component 110 and ventilation measurement component 120 are received by the end-tidal gas measurement component 130. The present invention contemplates implementing end-tidal gas measurement component 130 via processing unit 20 of FIG. 1. Characteristics of the received ventilation values are used by the end-tidal gas measurement component 130 to derive a more robust end-tidal gas value from the gas concentration values. For example, changes in the received ventilation values indicating the change from expiratory flow in the airway to inspiratory flow would be used to delineate in time the end of expiration. This may be obtained from the values of the flow, volume or surrogates thereof. For flow, the time of the zero crossing from expiratory flow (or zero flow in the case of a pause interval) to inspiratory flow may be used. For volume, the time from volume increasing (or flat) to decreasing may be used. Similarly, for acoustic measurements the change from expiratory to inspiratory flow can be determined by known methods.

Values from the ventilation measurement component 120 are also received by the ventilatory stability measurement component 140. The present invention also contemplates implementing ventilatory stability measurement component 140 via processing unit 20 of FIG. 1. Ventilatory stability may be determined by evaluating an historical record of ventilation values and assessing its stability. Time periods for assessment would vary based by the size of the gas stores of the gas in question. For $CO_2$ and $O_2$, the gas stores that would be considered are both the lung and blood stores. The time interval that would be assessed would be based upon size of those stores which could be estimated via methods as disclosed the '651 patent as well as rules of thumb based upon patient size. Exemplary methods of determining the variability of the ventilation values over the time period for assessment include analysis of the distribution of tidal volume values and, if a period of significant hyperventilation or hypoventilation is observed during the assessment period, then the end-tidal value would be deemed less reliable. The present invention also contemplates that the ventilatory stability measurement component 140 would receive values from the gas measurement component 110.

The estimates of ventilatory stability from the ventilatory stability measurement component 140 and the end-tidal values from end-tidal measurement component 130 are received by decision support system 150. The present invention further contemplates implementing decision support system 150 via processing unit 20 of FIG. 1. Using these values as well as other criteria, decision support system 150 determines the reliability of the end-tidal value. The reliability may be based simply on a threshold of ventilatory stability and may be indicated on the display of the host system numerically or graphically. The end-tidal number may be color coded to indicate its reliability such as red, yellow, green for unreliable, questionable, reliable, respectively. Based upon input from user or another system, decision support system 150 may be configured as a rule based system. For example, patient age as well as disease could permit physiological bounds (either fuzzy or hard bounds) to be used to indicate the reliability of the end-tidal value. It is also contemplated using measurement of Vd/Vt as noted earlier, in decision support system 150 to determine reliability of the end-tidal value. This could be simply an additional rule such as, in the case of Vd/Vt physiologic, if Vd/Vt physiologic >0.70 then the end-tidal $CO_2$ value is highly unreliable as surrogate of arterial $CO_2$.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of indicating a reliability of an end-tidal gas value comprising:
   measuring a plurality of gas concentration values;
   measuring a plurality of ventilation values;
   determining the end-tidal gas value from the plurality of gas concentration values;
   determining a degree of ventilatory stability from the plurality of ventilation values; and
   providing an estimate of the reliability of the end-tidal gas value using the degree of ventilatory stability.

2. The method of claim 1, wherein determining the end-tidal gas value is based, as least in part, on the plurality of ventilation values.

3. The method of claim 2, wherein determining the end-tidal gas value includes applying a mathematical relationship to the plurality of ventilation values and the plurality of gas concentration values.

4. The method of claim 3, wherein the mathematical relationship is a power regression.

5. The method of claim 1, wherein the measured plurality of gas concentration values comprises at least one of carbon dioxide, oxygen, nitrous oxide, nitric oxide, and anesthetic agents.

6. The method of claim 1, wherein the measured plurality of ventilation values comprises at least one of flow, volume, pressure, temperature, and humidity or any combination thereof.

7. A method of indicating a reliability of an end-tidal gas value comprising:
   measuring a plurality of gas concentration values;
   measuring a plurality of flow values;
   determining a plurality of volume values from the plurality of flow values;
   determining the end-tidal gas value from the plurality of gas concentration values;
   determining a degree of ventilatory stability from the plurality of flow values and the plurality of volume values; and
   providing an estimate of reliability of the end-tidal gas value using the degree of ventilatory stability.

8. The method of claim 7, wherein determining the end-tidal gas value is based, as least in part, on the plurality of flow values.

9. The method of claim 8, wherein determining the end-tidal gas value includes applying a mathematical relationship to the plurality of flow values and the plurality of gas concentration values.

10. The method of claim 9, wherein the mathematical relationship is a power regression.

11. The method of claim 7, wherein the measured plurality of gas concentration values comprises at least one of carbon dioxide, oxygen, nitrous oxide, nitric oxide, and anesthetic agents, and wherein the plurality of flow values comprises at least one of flow, volume, pressure, temperature, and humidity.

12. An apparatus for improving reliability of an end-tidal gas value comprising:
   means for sensing a plurality of gas concentration values;
   means for sensing a plurality of ventilation values;
   means for determining the end-tidal value from the plurality of gas concentration values;
   means for determining a degree of ventilatory stability from the plurality of ventilation values; and
   means for providing an estimate of the reliability of the end-tidal gas value using the degree of ventilatory stability.

13. The apparatus of claim 12, wherein the means for determining the end-tidal value determines the end-tidal gas value based, as least in part, on the plurality of ventilation values.

14. The apparatus of claim 13, wherein the means for determining the end-tidal gas value applies a mathematical relationship to the plurality of ventilation values and the plurality of gas concentration values.

15. The apparatus of claim 14, wherein the mathematical relationship is a power regression.

16. The apparatus of claim 12, wherein the sensed plurality of gas concentration values comprises at least one of carbon dioxide, oxygen, nitrous oxide, nitric oxide, and anesthetic agents, and wherein the sensed plurality of ventilation values comprises at least one of flow, volume, pressure, temperature, and humidity or any combination thereof.

17. An apparatus indicating a reliability of an end-tidal gas value comprising:
   means for measuring a plurality of gas concentration values;
   means for measuring a plurality of flow values;
   means for determining a plurality of volume values from the plurality of flow values;
   means for determining the end-tidal gas value from the plurality of gas concentration values;
   means for determining a degree of ventilatory stability from the plurality of flow values and the plurality of volume values; and
   means for providing an estimate of reliability of the end-tidal gas value using the degree of ventilatory stability.

18. The apparatus of claim 17, wherein the means for determining the end-tidal gas value determines the end-tidal gas value based, as least in part, on the plurality of flow values.

19. The apparatus of claim 17, wherein the measured plurality of gas concentration values comprises at least one of carbon dioxide, oxygen, nitrous oxide, nitric oxide, and anesthetic agents, and wherein the measured plurality of flow values comprises at least one of flow, volume, pressure, temperature, and humidity or any combination thereof.

* * * * *